(12) United States Patent
Chantriaux et al.

(10) Patent No.: US 8,088,112 B2
(45) Date of Patent: Jan. 3, 2012

(54) IMPLANTABLE MEDICAL SITE

(75) Inventors: Jean-François Chantriaux, Montauban (FR); Marie-Pierre Marthe Dieudonnée Chantriaux-de Wazieres, Montauban (FR)

(73) Assignee: Compagnie Europeenne d'Etude et de Recherche de Dispositifs pour l'Implantation par Laparoscopie, Vienne (FR)

( * ) Notice: Subject to any disclaimer, the term of this patent is extended or adjusted under 35 U.S.C. 154(b) by 586 days.

(21) Appl. No.: 11/573,929

(22) PCT Filed: Aug. 19, 2004

(86) PCT No.: PCT/FR2004/002161
§ 371 (c)(1),
(2), (4) Date: Jul. 30, 2007

(87) PCT Pub. No.: WO2006/027425
PCT Pub. Date: Mar. 16, 2006

(65) Prior Publication Data
US 2008/0119798 A1   May 22, 2008

(51) Int. Cl.
*A61M 37/00* (2006.01)
(52) U.S. Cl. .................................. 604/288.02
(58) Field of Classification Search .............. 604/6.16, 604/288.01–288.04, 891.1
See application file for complete search history.

(56) References Cited

U.S. PATENT DOCUMENTS

| 4,543,088 A * | 9/1985 | Bootman et al. ......... 604/288.02 |
| 4,710,174 A | 12/1987 | Moden et al. |
| 4,817,637 A * | 4/1989 | Hillegass et al. ............ 128/899 |
| 4,832,054 A * | 5/1989 | Bark ............................. 128/899 |
| 4,857,053 A * | 8/1989 | Dalton ................... 604/288.02 |
| 5,352,204 A * | 10/1994 | Ensminger ............. 604/288.03 |
| 2003/0120288 A1* | 6/2003 | Benchetrit .................... 606/151 |
| 2004/0082908 A1* | 4/2004 | Whitehurst et al. ............ 604/67 |

FOREIGN PATENT DOCUMENTS

| FR | 2851168 | 8/2004 |
| WO | WO01/12158 | 2/2001 |

* cited by examiner

*Primary Examiner* — Theodore Stigell
(74) *Attorney, Agent, or Firm* — Jason A. Berstein; Barnes & Thornburg LLP

(57) ABSTRACT

An implantable device (1) for injecting and/or drawing fluid either in an organ or vessel of the body of a human or animal patient and the device comprising a housing (2) with a chamber (2A) connected to a catheter, the catheter is connected either to the organ or vessel or to the compartment. The housing (2) has a proximal wall (4) and a distal wall (5) between which a lateral wall extends. The housing (2) has a puncture area (7) able to be pierced by a hollow needle (14) for injecting and/or drawing fluid in the chamber (2A). The puncture zone (7) extends on the proximal wall (4) and the lateral wall.

8 Claims, 4 Drawing Sheets

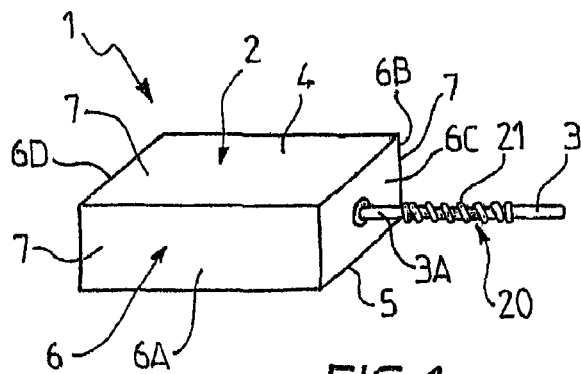
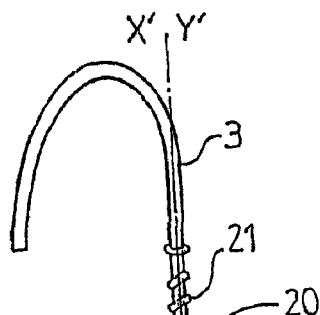
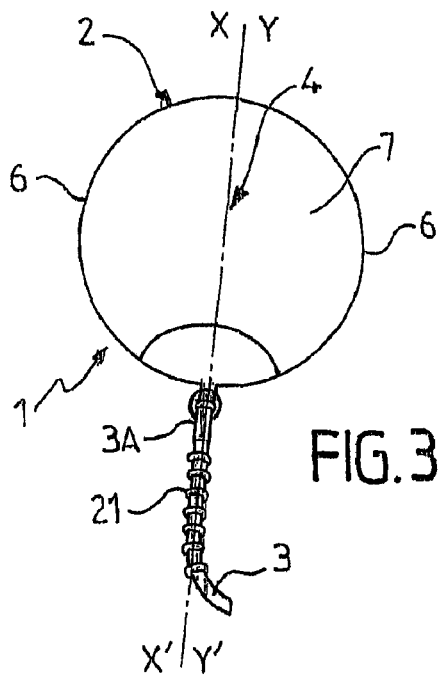
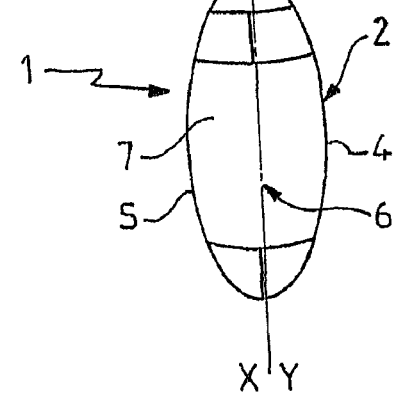
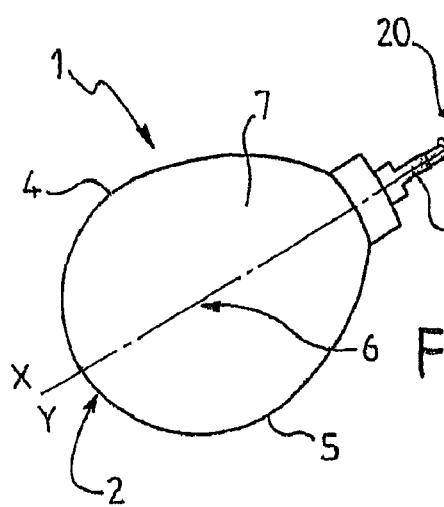

IMPLANTABLE MEDICAL SITE

PRIORITY CLAIM

This patent application is a U.S. National Phase of International Application No. PCT/FR2004/002161, filed Aug. 19, 2004, the disclosure of which is incorporated herein by reference in its entirety.

FIELD OF THE INVENTION

The present invention relates to devices for surgically inserting under the skin of a human or animal patient capable of being pierced subsequently by a hollow needle through the skin of the patient to introduce and/or extract substances into or from the body of the patient while limiting repeated cutaneous trauma at the same location. Such devices are generally referred to as implantable sites or as access ports.

The present invention relates more particularly to an implantable device for injecting and/or extracting fluid either into or from an organ or a vessel of the body of a human or animal patient, or into or from an inflatable and/or deflatable compartment of a surgical implant.

BACKGROUND OF THE INVENTION

Known implantable sites are generally in the form of a housing including an end wall with extending side walls having free ends defining a proximal opening.

The end wall and the side walls are made of solid and rigid material, such as titanium, to ensure that the end wall and the side walls cannot be pierced by a needle. The proximal opening is closed by a substantially plane membrane of self-sealing material, thus forming a "septum". Although the devices are generally satisfactory, they nevertheless present significant drawbacks.

Although the known devices are relatively bulky and potentially uncomfortable for the patient, the known devices provide an injection area that is small, thus exposing the surrounding tissue to risks of lesions by perforation since the probability of the practitioner piercing away from the "septum" is significant.

Furthermore, the known devices are liable to turn over under the skin as a result of movement by the patient. In extreme circumstances, the site can be turned 180°, thereby totally masking or occluding the "septum". The device as turned over in this way becomes unusable requiring new surgery to implant a new device.

Proposals have been made to bind the site to surrounding biological tissues in an effort to keep the site from turning over. Known devices are provided with holes that enable the devices to be sutured to neighboring biological tissues.

This solution is unsatisfactory since the solution requires a relatively large surgical approach path, requires surgery that is longer and more difficult, and increases patient discomfort and the risk of infection.

SUMMARY OF THE INVENTION

The features provided by the present invention address the various drawbacks mentioned above and provide a novel implantable fluid injection and/or extraction device and a method for implanting the device and injecting and/or extracting fluid.

Another feature of the present invention provides a novel implantable fluid injection and/or extraction device to pierce the skin using a technique that is substantially similar to the technique implemented when piercing a natural vein.

Another feature of the present invention provides a novel implantable fluid injection and/or extraction device that reduces the risks and drawbacks associated with body movements of the patient.

Another feature of the present invention provides a novel implantable fluid injection and/or extraction device that does not need to be sutured to the body of the patient.

Another feature of the present invention provides a novel implantable fluid injection and/or extraction device of particularly simple and compact design.

Another feature of the present invention provides a novel implantable fluid injection and/or extraction device that is particularly lightweight.

Another feature of the present invention provides a novel implantable fluid injection and/or extraction device that is particularly reliable.

The features provided by the present invention are achieved by an implantable device for injecting and/or extracting fluid either into or from an organ or vessel of the body of a human or animal patient or into or from an inflatable and/or deflatable compartment of a surgical implant, the device comprising in one exemplary embodiment, a housing within which there is formed a chamber designed to be connected to a catheter, the catheter itself being designed to be connected either to the organ or vessel or to the compartment, the housing comprising a proximal wall and a distal wall with a side wall extending between them, the housing including a puncture zone designed to be capable of being pierced by a hollow needle in order to inject and/or extract fluid into or from the chamber, the device being characterized in that the puncture zone is shaped in such a manner as to extend simultaneously at least over the proximal wall, and the side wall.

BRIEF DESCRIPTION OF THE DRAWINGS

Other features and advantages of the present invention become apparent on reading the following description with reference to the drawings, given in purely illustrative and non-limiting manner.

FIG. 1 is a perspective view of a first exemplary embodiment of the device of the present invention;

FIG. 2 is a perspective view of a second exemplary embodiment of the device of the present invention;

FIG. 3 is a perspective view of a third exemplary embodiment of the device of the present invention;

FIG. 4 is a perspective view of a fourth exemplary embodiment of the device of the present invention;

FIG. 5 is a perspective view showing a fifth exemplary embodiment of the device of the present invention;

DETAILED DESCRIPTION OF THE INVENTION

Figure 6:
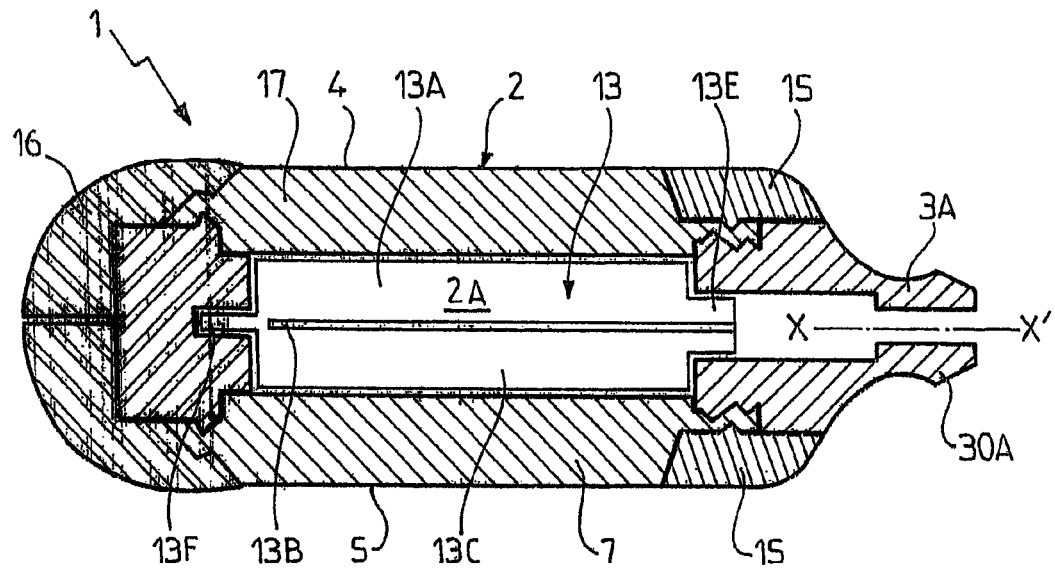
FIG. 6 is a longitudinal section view showing a sixth exemplary embodiment of the device of the present invention.

The present invention relates to an implantable fluid injection and/or extraction device 1, which can also be referred to as an "implantable site", that is surgically implanted in the body of a patient, and in particular under the skin of the patient, to create an access port for injecting and/or extracting fluids into or from the body of the human or animal patient.

The implantable device 1 of the present invention can be implemented and adapted to a variety of uses.

Firstly, the implantable device 1 of the present invention may be designed for injecting and/or extracting fluid into or from an organ or a vessel of the body of a patient, and in particular in the venous and/or arterial system of the patient. In this application, the device 1 of the present invention allows medication to be injected into a vein or an artery.

The device 1 of the present invention may also be adapted to feed implanted reservoirs of the insulin pump or antalgic type.

In another exemplary embodiment unknown in the prior art, the device 1 of the present invention is adapted to form an artificial vein (or artery) that a practitioner, a doctor, or a nurse can pierce like a natural vein for injecting medication or taking blood.

The implantable device 1 of the present invention may also be adapted to injecting and/or extracting fluid into or from an implantable and/or deflatable compartment of a surgical implant, and in particular a gastroplasty ring for treating obesity.

Such a gastric ring is known in the art and is generally formed by a flexible strip designed to be closed in a loop around the stomach substantially towards and at its two ends, using a closure system to reduce the diameter of the aperture of the stoma. The strip may include an annular compression chamber of adjustable volume connected by a catheter to the implantable device 1 of the present invention thus enabling the pressure inside the chamber to be adjusted so as to adjust the diametral expansion of the chamber.

The device of the present invention may be used for adjusting other surgical implants, e.g., such as balloons or artificial sphincters.

Below, reference is made more particularly to a hypodermic device, i.e., a device designed to be positioned immediately under the skin of the patient. The device of the present invention could also be implanted at other locations within the body of the patient, and in particular at greater depth.

According to the present invention, the device 1 comprises a housing 2 within which there is a chamber 2A substantially hermetically closed and leaktight. The chamber 2A is connected to a catheter 3, the catheter 3 is connected either to an organ or vessel 10 into which the catheter injects fluid or from which the catheter takes fluid (cf. FIG. 11), or else to an inflatable/deflatable compartment of a surgical implant (not shown).

According to the present invention, the housing 2 has a proximal wall 4 and a distal wall 5, wherein a side wall 6 extends between the proximal wall 4 and the distal wall 5. The term "proximal" conventionally designates the wall that is situated immediately under skin of the patient once the device has been implanted subcutaneously.

In a conventional manner, the housing 2 includes a puncture zone 7 capable of being pierced by a hollow needle 14, to inject and/or extract fluid into or from the chamber 2A.

Advantageously, the puncture zone 7 comprises a self-sealing membrane, e.g., made of an elastomer material of the silicone type. The membrane presents "self-healing" properties wherein the orifice created when the membrane is pierced by the needle 14 closes automatically after the needle 14 is extracted, thereby enabling the chamber 2A to remain substantially leaktight. The puncture zone 7 extends simultaneously over the proximal wall 4 and the distal wall 5.

Unlike prior art devices in which the puncture zone extends only over a portion of the proximal wall requiring the device 1 to be firmly sutured to the surrounding tissues, the puncture zone 7 of the present invention extends to the side wall 6 so that the device 1 does not need to be secured by a suture.

If the device 1 of the present invention turns over, e.g., under the effect of movements of the patient, there is a reduced probability that the puncture zone 7 will be inaccessible because the puncture zone 7 extends over both the proximal wall 4 and the side wall 6.

In a first exemplary embodiment, shown in FIG. 1, the proximal, distal, and side walls 4, 5, and 6 combine to form a surface that is substantially polyhedral.

More particularly, in the example of FIG. 1, proximal, distal, and side walls 4, 5, and 6 form a rectangular parallelepiped. Under such circumstances, the side wall 6 is formed firstly by two parallel longitudinal panels 6A, 6B and secondly by two parallel transverse panels 6C, 6D, the transverse panels 6C, 6D extending in a direction substantially perpendicular to the direction in which the longitudinal panels 6A, 6B extend.

Advantageously, the catheter 3 is connected to the chamber 2A through one of the transverse panels 6C, 6D via a duct 3A connecting the chamber 2A to the outside of the device 1 and extending longitudinally substantially in the same direction as the longitudinal panels 6A, 6B.

Advantageously, the puncture zone 7 extends over the major portion, or even substantially the totality of the proximal and distal walls 4 and 5 and the longitudinal panels 6A, 6B. The transverse panels 6C, 6D could naturally also constitute part of the puncture zone 7, although that is not really necessary, given there is little risk of the device 1 turning about the transverse direction. Thus, all of the faces of the housing 2 shown in FIG. 1 can advantageously be used for puncturing, such that accidental turning over of the device 1 does not lead to troublesome consequences for the practitioner or the patient.

The alternate exemplary embodiments of FIGS. 2-8 are described in greater detail below.

In the various exemplary embodiments shown in FIGS. 2-8, the duct 3A connecting the chamber 2A to the outside of the device 1 and for connection to the catheter 3 extends longitudinally along a first axis X-X'.

In order to establish a reliable mechanical connection between the duct 3A and the catheter 3, the duct 3A may be provided with a coaxial swelling 30A (cf. FIGS. 6 and 7) of diameter slightly greater than the nominal inside diameter of the catheter 3. Conventionally, the catheter 3 presents a certain amount of radial elasticity and is engaged by force on the duct 3A and the swelling 30A, which serves to hold the catheter.

It is also possible to clamp the catheter 3 onto the duct 3A by means of a clamping ring.

Advantageously, the catheter 3 is surrounded, in the vicinity of the duct 3A, with stiffener means 20 (cf. FIGS. 1-5), e.g., constituted by a helical wire or tube 21 like a spring.

The stiffener means 20, which may present a certain amount of flexibility in bending, serve to avoid accidental closing of the catheter 3 by the catheter 3 kinking.

According to the exemplary embodiments of FIGS. 2-8, the proximal, distal, and side walls 4, 5, and 6 are shaped and arranged in such a manner that the housing 2 is substantially symmetrical about a second axis Y-Y', the second axis Y-Y' is substantially parallel to the first axis X-X'.

The housing 2 presents circular symmetry about a second axis Y-Y' that extends substantially in the same direction as the duct 3A for connection to the catheter 3. Under such circumstances, because of the axial symmetry of the housing 2, the proximal, distal, and side walls 4, 5, and 6 run substantially into one another and form a single surface of revolution.

Advantageously, the proximal, distal, and side walls 4, 5, and 6 form a surface that is substantially spherical, as shown in FIG. 3. In this configuration, the puncture zone 7 may extend substantially over all of the proximal, distal, and side walls 4, 5, and 6, i.e., over substantially the entire spherical surface. Nevertheless, without going beyond the ambit of the invention, provision could be made for the puncture zone 7 to extend only over a central circular zone of the spherical surface, the circular zone being symmetrical about the second axis Y-Y', which preferably coincides with the first axis X-X'.

In another exemplary embodiment, shown in FIG. 2, the proximal, distal, and side walls 4, 5, and 6 form a surface that is substantially ovoid, extending longitudinally along the axis Y-Y' in the same direction as the duct 3A.

The ovoid housing is particularly easy to insert under the skin of the patient, and is particularly well tolerated by the patient.

As with the spherical housing shown in FIG. 3, the puncture zone 7 of the ovoid housing of FIG. 2 may extend substantially over the entire surfaces of the proximal, distal, and side walls 4, 5, and 6, i.e., over the entire ovoid surface. In a preferable configuration, the puncture zone 7 occupies only a central circular zone of the ovoid surface, the circular zone being symmetrical about the second axis Y-Y'.

In the variant shown in FIG. 4, the proximal, distal, and side walls 4, 5, and 6 form a surface that is substantially pear-shaped.

Preferably, the duct 3A connects the catheter 3 to the chamber 2A by means of the tip of the pear-shaped surface.

Advantageously, the puncture zone 7 can extend over substantially the entire area of the proximal, distal, and side walls 4, 5, and 6, or the puncture zone 7 may occupy merely a portion of the pear-shaped surface, and for example, and as described for the above exemplary embodiments, the puncture zone 7 may occupy only a central circular zone about the axis of symmetry Y-Y'.

In another exemplary embodiment, shown in particular in FIGS. 5-8, the proximal, distal, and side walls 4, 5, and 6 form a surface that is substantially cylindrical. The puncture zone may extend over substantially all of the cylindrical surface, or over only a portion of the surface, and in particular a central circular zone.

Advantageously, the housing 2 corresponding to the exemplary embodiment shown in FIG. 6 has a front ring 15 and a rear ring 16 facing each other and spaced apart, being coaxial about the first and second axes X-X' and Y-Y'. Between the rings 15, 16 is a cylindrical sleeve 17 made of elastomer material and forming the puncture zone 7. The duct 3A is engaged in the front ring 15, so as to be centered relative to the axis Y-Y'.

The front and rear rings 15 and 16 may optionally be interconnected mechanically by spacers (not shown) enabling the sleeve 17 to be maintained under longitudinal compression stress. In order to obtain this compression prestress effect, the sleeve 17 preferably is slightly longer than the distance between the front and rear rings 15 and 16. The sleeve 17 is then inserted by force between the two rings, thereby setting up compression in the elastomer material along the axis Y-Y', which coincides in these examples with the axis X-X'.

Figure 7:
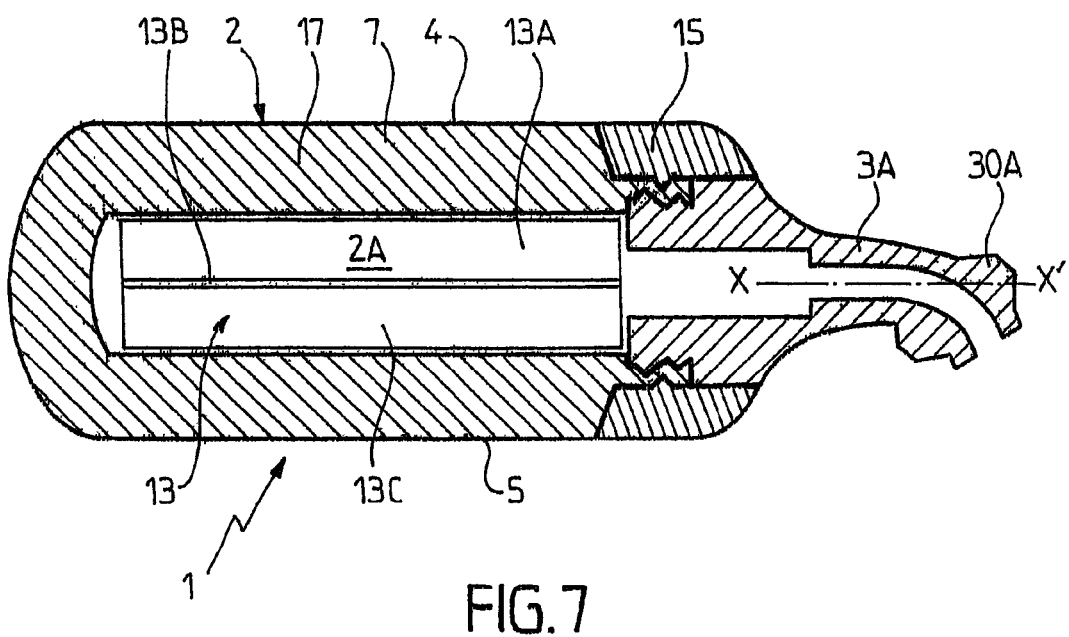
FIG. 7 is a longitudinal section view showing a seventh exemplary embodiment of the device of the present invention.
Figure 8:
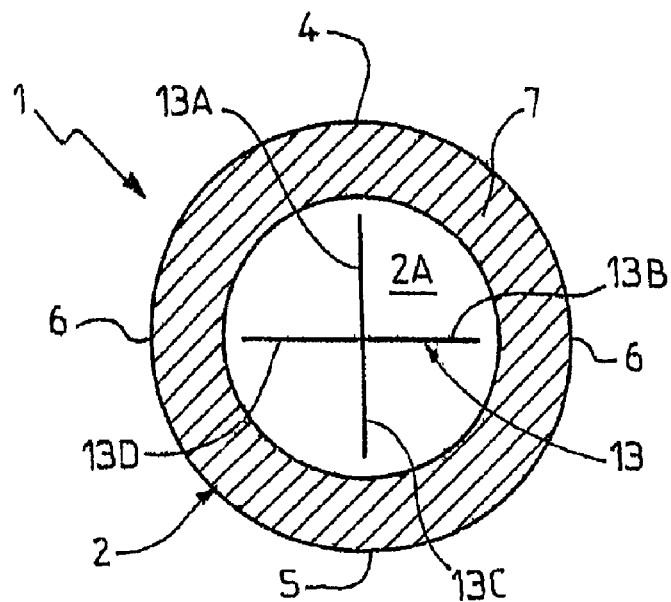
FIG. 8 is a cross-section view showing the exemplary embodiments of the device in FIGS. 6 and 7.

It is also possible, as shown in FIG. 7, to envisage that the housing 2 includes only one distinct ring, i.e., the front ring 15, the rear ring being made integrally with the sleeve 17.

Advantageously, the region of the sleeve 17 that corresponds to the rear ring 16 can be made of an elastomer material that is different from the material from which the remainder of the sleeve is made, for example, material that presents greater hardness.

Figure 10:
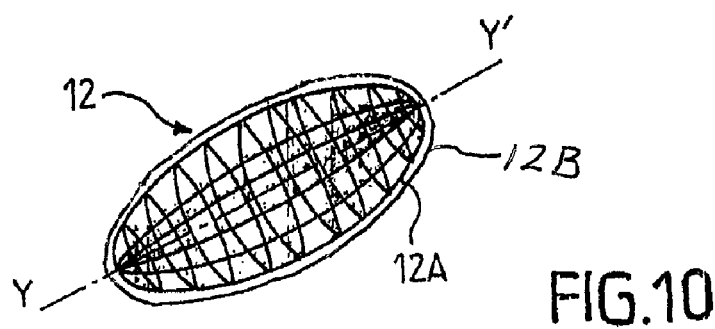
FIG. 10 is a perspective view showing the internal structure of the device shown in FIG. 2.

Advantageously, and regardless of the embodiment involved, the housing 2 of the present invention may be a frame 12 made of a material that is substantially not pierceable by a needle 14 (cf. FIG. 10). The frame 12 is advantageously covered by an envelope 12B made of a self-sealing material, the frame 12 having openings to form the puncture zone 7 in cooperation with the envelope. More particularly, the frame 12 is designed to give the general shape to the housing 2, specifically an ovoid shape for the example shown in FIG. 10. The frame 12 supports an envelope in the form of a substantially elastic pouch suitable for being engaged over the frame 12 and for taking up the general shape of the frame 12, like a sock. The envelope may advantageously comprise a membrane of elastomer material of the biomedical silicone type.

The frame 12 is perforated, at least locally, by a series of orifices of sufficient size to allow the needle 14 to pass through. After initially piercing the envelope, the needle can reach the internal volume defined by the frame 12 and corresponding to the chamber 2A.

Advantageously, the frame 12 is a lattice of rigid material, as shown in FIG. 10. For example, the lattice may be made of titanium wires, or the lattice may be obtained by molding a plastics material.

Figure 9:
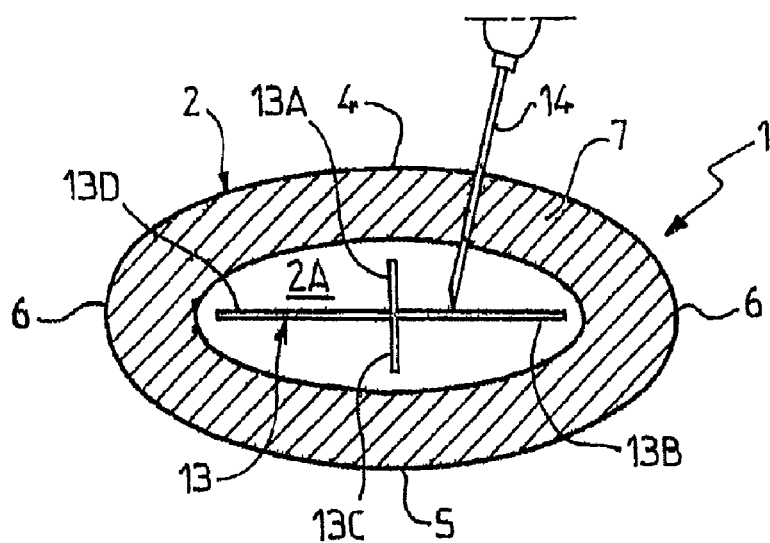
FIG. 9 is a cross-section view showing an eighth exemplary embodiment of the device of the present invention.

Above, housings 2 are described that present circular symmetry about the second axis Y-Y' that is parallel to or coincides with the first axis X-X'. Nevertheless, without going beyond the ambit of the present invention, it is possible to envisage that the housing 2 is not genuinely circularly symmetrical but is merely formed by a curved or warped surface, e.g., of elliptical section, as shown in FIG. 9.

Advantageously, and as shown in FIGS. 6-9, a screen 13 made of material that is not pierceable by the needle 14 is placed within the chamber 2A to prevent the housing being pierced through by the needle 14.

The screen 13 acts as an abutment for the needle 14. In particular, the screen 13 should be in the shape of the puncture zone 7 to ensure that the puncture zone 7 can be pierced effectively and reliably at any point.

Advantageously, the screen 13 comprises a bladed wheel shaped and positioned in such a manner that the blades 13A, 13B, 13C, and 13D extend substantially radially about the axis of symmetry Y-Y' of the housing 2.

Advantageously, the blades number at least four and are regularly spaced apart angularly. It is possible for the number of blades to be greater or smaller, or indeed to provide some other type of screen 13.

The screen 13 is shaped to allow fluid communication and circulation within the chamber 2A.

For example, where the screen 13 is formed by a wheel having four blades 13A, 13B, 13C, and 13D, the four compartments defined within the chamber 2A by the blades 13A, 13B, 13C, and 13D are not sealed relative to one another and are all in fluid communication with one another, even if indirectly. It is possible, for example, to ensure that the blades are of a size that ensures they do not fit closely against the walls of the housing 2.

The screen 13 may slope freely within the chamber 2A, or it might be held in position using a specific fastener system. The fastener system could, for example, comprise centering shafts 13E, 13F (cf. FIG. 6) cooperating with complementary recesses formed within the housing to hold the bladed wheel in position while allowing the bladed wheel to turn about the axis Y-Y'.

The use of a screen 13 is optional.

Figure 11:
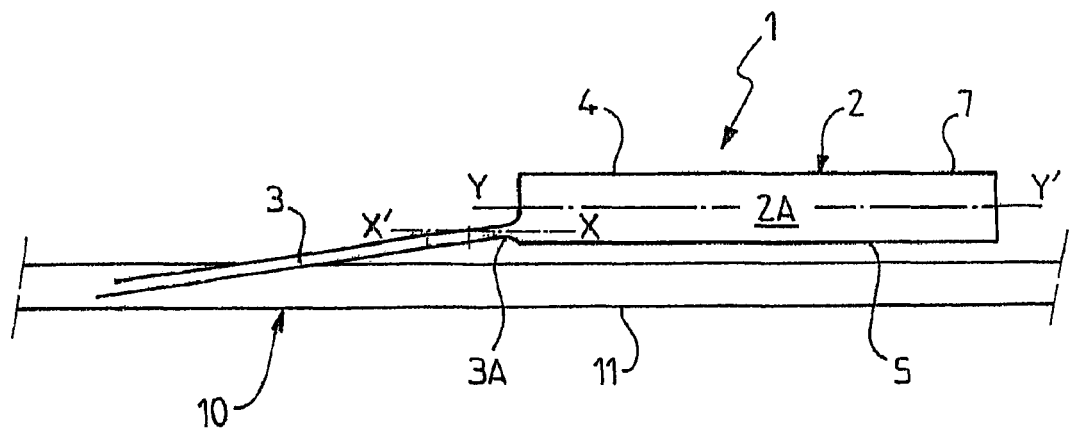
FIG. 11 is a side view showing a ninth exemplary embodiment of the device of the present invention forming an artificial vein.
Figure 12:
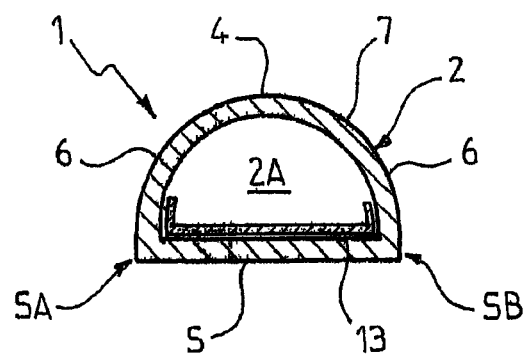
FIG. 12 is a cross-section view of the device of the present invnetion shown in FIG. 11.

Following is a description in greater detail of the alternate exemplary embodiment shown in FIGS. 11 and 12 relating to a hypodermic device 1 for injecting medication into a vein 11 (or an artery) and/or for taking blood from the vein 11 (or artery), the device 1 forming an artificial vein or artery.

The device 1 of this alternate exemplary embodiment imitates a natural vein for injecting medication intravenously or for taking blood.

The device 1 substantially reproduces the shape of a portion of a natural vein, i.e., the device 1 is an elongate tubular housing, e.g., made entirely out of a pierceable material of the silicone type.

The device 1 lies flush under the skin of the patient, above the vein 11 to which the device 1 is connected.

The device 1 of this alternate exemplary embodiment is pierced in the same manner as a natural vein, i.e., at a grazing angle relative to the skin of the patient, and not perpendicularly as when piercing a prior art site. Such "tangential" piercing means that the presence of the screen 13 is not absolutely necessary.

Nevertheless, such a screen can be envisaged, as is shown in the exemplary embodiments of FIGS. 11 and 12.

In this alternate exemplary embodiment, the distal wall 5 is substantially plane and is defined laterally by two side edges 5A, 5B, while the proximal wall 4 and the side wall 6 form a surface of revolution, e.g., semicircular, interconnecting the side edges 5A, 5B.

The screen 13 is a gutter made of a material that cannot be pierced by the needle 14 but that is preferably flexible. The gutter advantageously presents a channel section, with the web on the channel section resting in the chamber 2A on the distal wall 5, while the flanges of the channel section are upstanding against the side wall 6.

The concept of an artificial vein developed in the ambit of the present invention presents a feature that is independent of the other applications mentioned above.

Finally, it should be observed that the housing 2 may advantageously be radio-opaque, by including an appropriate marker substance in its internal structure, either uniformly or otherwise.

The present invention can be used in making and using implantable sites for injecting and/or extracting fluid.

The invention claimed is:

1. An implantable device for injecting and/or extracting fluid either into or from an organ or vessel of the body of a human or animal patient, or into or from an inflatable and/or deflatable compartment of a surgical implant, the device comprising:
   a) a housing having a chamber defined by a proximal wall and a distal wall with a side wall extending therebetween, the housing including a puncture zone designed to be capable of being pierced by a hollow needle in order to inject and/or extract fluid into or from the chamber, the chamber being connectable to a catheter;
   b) a screen made of a material that is not pierceable by the hollow needle, the screen being disposed within the chamber so that the hollow needle puncturing the proximal wall in the puncture zone is blocked by the screen from extending through the chamber and puncturing the distal wall generally on the housing generally opposite from the site of the proximal wall,
   wherein the device is adapted to rotate within the organ or vessel once implanted,
   wherein the distal wall, proximal wall and side walls are puncturable by the hollow needle,
   wherein the puncture zone is shaped so as to extend simultaneously at least over the proximal wall the side wall, and the distal wall,
   and, wherein the housing further comprises a frame made of a material that is substantially not pierceable by the hollow needle, the frame having at least one opening, substantially the entire frame being covered by at least one pierceable envelope made of a self-sealing material.

2. The implantable device of claim 1, wherein the puncture zone, chamber and at least one wall are adapted for receiving a needle inserted therein.

3. The implantable device of claim 1, wherein the distal wall includes a self-sealing portion.

4. The implantable device of claim 1, wherein the screen is sufficiently spaced from the distal wall to allow the insertion of a needle tip therebetween.

5. The implantable device of claim 1, wherein the frame has a plurality of openings defined therein which can accommodate the hollow needle.

6. The implantable device of claim 1, further comprising a catheter connectable to the housing.

7. An implantable device for injecting and/or extracting fluid either into or from an organ or vessel of the body of a human or animal patient, or into or from an inflatable and/or deflatable compartment of a surgical implant, the device comprising:
   a) a housing having
      (i) a frame made of a material that is substantially not pierceable by the needle, the frame having at least one pierceable opening defined therein, substantially the entire frame being covered by at least one envelope made of a self-sealing material,
      (ii) a chamber defined by a proximal wall and a distal wall and a side wall extending therebetween, the distal wall, proximal wall and side wall being puncturable by a needle, and
      (iii) a puncture zone designed to be capable of being pierced by a needle in order to inject and/or extract fluid into or from the chamber, the puncture zone being shaped so as encompass at least a portion of the proximal wall, the distal wall and the side wall; and,
   b) a screen made of a material that is not pierceable by the needle, the screen being disposed within the chamber so that the needle puncturing a first location in the puncture zone is blocked by the screen from puncturing a second location in the puncture zone generally on the housing generally opposite from the site of the first location,
   wherein the device is adapted to rotate within the organ or vessel once implanted, and,
   wherein the chamber is connectable to a catheter.

8. The implantable device of claim 7, further comprising a catheter connectable to the housing.

* * * * *